United States Patent [19]

Frank

[11] Patent Number: 5,006,401
[45] Date of Patent: Apr. 9, 1991

[54] COMPOSITE COMPRESSION AND SUPPORT DRESSING

[75] Inventor: Margaret A. Frank, Lawrenceville, N.J.

[73] Assignee: E. R. Squibb & Sons, Inc., Princeton, N.J.

[21] Appl. No.: 275,298

[22] Filed: Nov. 23, 1988

[51] Int. Cl.⁵ .............................................. D03D 3/00
[52] U.S. Cl. ...................................... 428/231; 128/156; 428/230; 428/246; 428/343; 428/355; 428/356; 428/40
[58] Field of Search ................. 128/156; 428/343, 355, 428/260, 230, 231, 356, 246, 40

[56] References Cited

U.S. PATENT DOCUMENTS

| | | | |
|---|---|---|---|
| 4,302,500 | 11/1981 | Flora | 428/284 |
| 4,377,160 | 3/1983 | Romaine . | |
| 4,538,603 | 9/1985 | Pawelchak et al. . | |
| 4,551,490 | 11/1985 | Doyle et al. . | |
| 4,630,603 | 12/1986 | Greenway | 428/284 |
| 4,699,133 | 10/1987 | Schafer et al. . | |
| 4,743,499 | 5/1988 | Volke | 428/355 |
| 4,784,653 | 11/1988 | Bolton | 428/355 |

Primary Examiner—James J. Bell
Attorney, Agent, or Firm—Theodore R. Furman, Jr.

[57] ABSTRACT

In accordance with the present invention a novel composite compression and support dressing is disclosed. This dressing comprises an extensible bandage having a stretchable hydrocolloid adhesive composition laminated thereto.

12 Claims, 1 Drawing Sheet

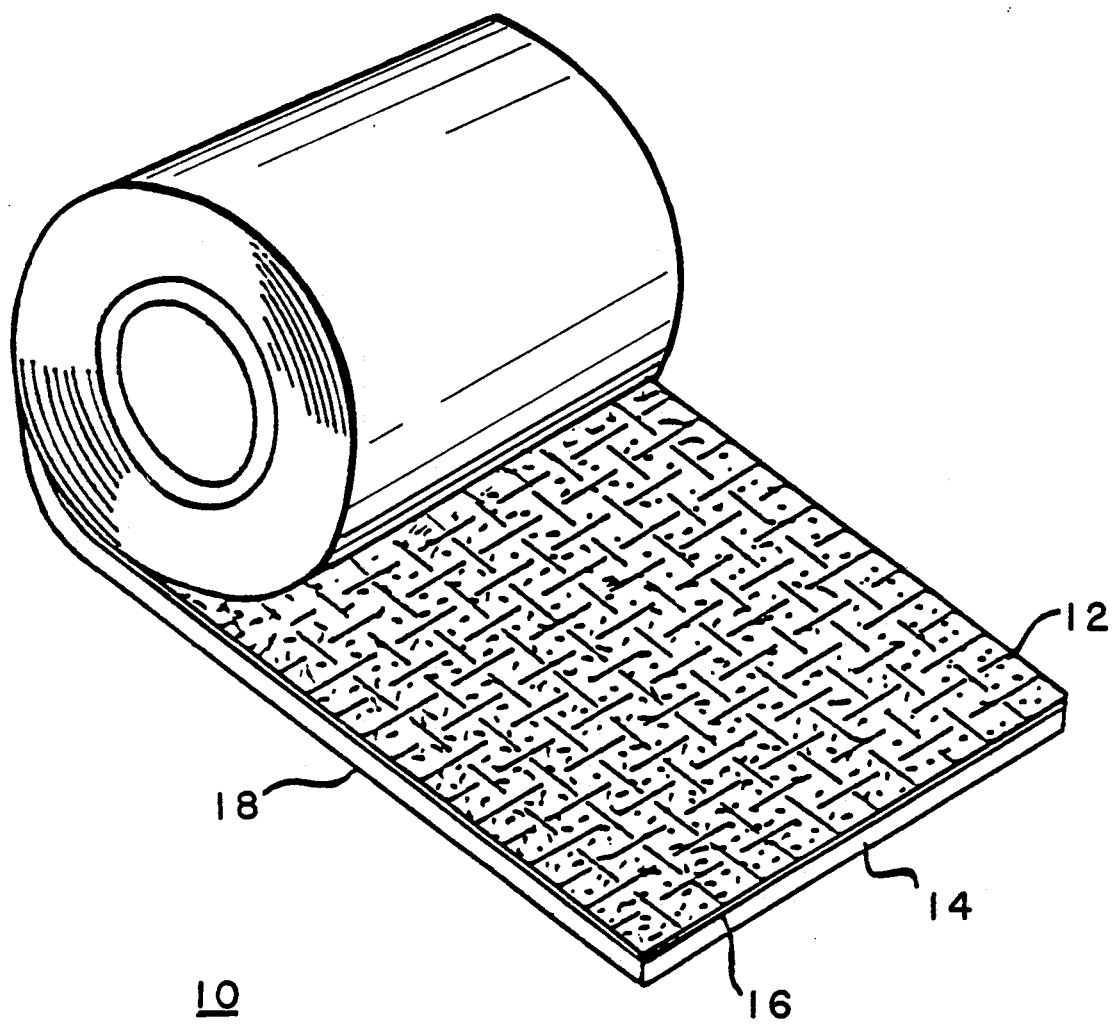

COMPOSITE COMPRESSION AND SUPPORT DRESSING

FIELD OF THE INVENTION

The present invention relates to an occlusive extensible compression bandage and is more particularly concerned with such a dressing for use in wound care and leg ulcer treatment.

BACKGROUND OF THE INVENTION

Compression and support dressings are widely known for use in a variety of medical purposes. A particular area where compression dressings are considered important is in the care and treatment of venous stasis leg ulcers.

For example, venous stasis leg ulcers are believed to be the result of venous insufficiency, i.e., incompetent vein perforator valves, in the leg. One main focus of treatments for leg ulcers is the dermatological care. Indeed, many workers in this area feel that care to the surrounding skin of the leg and protection of the epithelium (delicate healing area directly peripheral to the ulcer) are crucial to successful treatment of leg ulcers. Care to the surrounding skin includes treatment of psoriatic conditions which often accompany leg ulcers, avoidance of skin sensitization from agents in the dressing, prevention of skin maceration and preventing damage from the ulcer exudate.

The mainstay, however, of nearly all venous stasis leg ulcer treatments is the application of compression. Elasticated bandages, and the like, have been extremely suitable for this purpose. Properly applied compression is thought to enhance circulation and thereby alleviate at least some of the cause of the venous stasis ulcers. These compression bandages also serve to keep the desired gauze or primary dressing flatly and firmly in place over the ulcer.

Typical extensible bandages suitable for compression include adhesive rubber bandages (e.g., Elastic PEG from Becton Dickinson; Elastoplast from Beiersdorf, Inc., Elasti Kon from Johnson & Johnson; Conform Elastic Tape from Kendall; Flexoplast from Edward Taylor Ltd.; Coban from 3M), plain cotton bandages (e.g., Tomac from American Hospital Supply; Dixie from Chaston Medical), cotton bandages reinforced with Lycra/Spandex (e.g., Ace Bandage from Becton Dickinson; Elastic Bandage from Conco Medical; Turniwrap from Richards Mfg.; Elastic Bandage from Edward Weck & Sons), cotton reinforced with rubber (e.g., Dynaflex from Johnson & Johnson; Ace Centur from Becton Dickinson, and the like), tubular open netted elastic (e.g., Spandage Stretch from Medi Tech Int'l), cotton conforming bandages, cotton crêpe bandages, elastic adhesive bandages (which may include zinc oxide), and the like.

Some extensible bandages known in the art also include ravel-resistant side edges and may include an adhesive on one or both major surfaces so as to be self-adhesive or adhesive to the skin of the wearer. One major importance of using an adhesive has been that it can reduce the slippage of the wrapped compression bandage while the patient moves, thereby providing more uniform support and compression for extended periods of time.

U.S. Pat. No. 4,699,133 to Schafer et al. describes a self-adhesive support bandage which is air and moisture permeable. Small adhesive particles are applied only to the raised fiber edges of the bandage so that adhesion to skin and hair is avoided.

Also useful in the treatment of venous leg ulcers are the impregnated paste type bandages. These are typically in the form of a tape (Viscopaste PB7) or conformal boot (Unna's Boot) which are impregnated with zinc paste and the primary purpose of these dressings is to soothe the surrounding skin.

Additional support can be provided by securing-type dressings, such as Tubigrip, which are employed to keep the other articles in place when combinations of products are employed. In fact, the most widely accepted methods for treating venous leg ulcers utilize several of the above-described products in combination. For example, the gauze or primary wound dressing can be placed over the ulcer and is then wrapped or covered with a paste type dressing. This is followed with a compression bandage and optionally with a securing-type bandage.

Although this combination has been relatively effective, it is not without drawbacks. Primarily, it comprises three or four separate elements which becomes expensive, bulky and very time consuming for the caregiver. If the paste bandage is eliminated, the surrounding skin is not adequately cared for, and if the securing bandage is eliminated, slippage of the various components is likely to occur.

SUMMARY OF THE INVENTION

In accordance with the present invention a novel composite compression and support dressing is disclosed. This dressing comprises an extensible compression and support bandage having a stretchable hydrocolloid adhesive composition laminated thereto. In a preferred embodiment, the adhesive composition comprises a homogeneous blend of mineral oil, one or more polyisobutylenes or mixtures of one or more polyisobutylenes and an elastomer such as butyl rubber, styrene radial or block type copolymers, water soluble hydrocolloid gums, water swellable cohesive strengthening agents, tackifiers, and small amounts of various other optional ingredients.

BRIEF DESCRIPTION OF THE DRAWING

The FIGURE shows the composite compression and support dressing of the present invention.

DETAILED DESCRIPTION OF THE PRESENT INVENTION

This invention is directed to a composite compression and support dressing which performs the dual function of providing skin and wound care, as well as compression and support. The present invention utilizes a medical grade hydrocolloid adhesive composition which is pressure sensitive and preferably is highly resistant to erosion from wound and body fluids and is useful in the treatment of skin lesions and burns. Adhesives of this variety are disclosed in U.S. Pat. No. 4,551,490 to Doyle et al. and in U.S. Pat. No. 4,538,603 to Pawelchak et al. Doyle described adhesives for stomal and incontinence applications and Pawelchak disclosed a wound dressing employing a similar adhesive. These, and similar adhesives, and variations thereof, have good wound care properties, can stand up to wound or ulcer exudate and are stretchable. These adhesive compositions are considered fluid-interactive since they (1) are resistant to wound and body fluids, such as wound exudate, perspiration and the like, and, (2) can swell to absorb substantial amounts of such fluids. This fluid-interactive quality renders the dressings of the present invention very useful in protecting surrounding skin from wound or ulcer exudate and in adhering to moist surfaces.

By laminating such adhesives to one side of a standard extensible bandage a highly useful wound and ulcer product is provided.

Referring to the FIGURE there is shown a composite compression and support dressing 10 in the form of a ribbon-type roll article. This dressing 10 is conveniently simultaneously unrolled and wrapped onto the appropriate body part as is known with other such roll bandages. The dressing 10 includes an extensible bandage 12 having a thin hydrocolloid adhesive composition 14 laminated thereto. An optional thin latex layer 16, interposed the bandage 12 and adhesive composition 14, provides cohesive strength for the dressing 10. An optional release paper 18 overlies the skin contacting surface of the adhesive composition 14. It should be understood that the dressing of the present invention could be rolled opposite of that depicted in the FIGURE, and further that the dressing need not be rolled at all.

The composite compression and support dressing of the present invention is very useful, for example, in the treatment of venous leg ulcers. This is because the dressing can in many instances be used as the sole treatment. By appropriate wrapping of the dressing around the leg, wound care, skin care for the surrounding skin, occlusion and adhesion are all provided by the hydrocolloid adhesive composition and compression and support are provided by the extensible bandage laminated thereto. Essentially all of the elements of proper leg ulcer care are achieved in one easy step with just one dressing. This makes treatment much more simplified for the caregiver. Additionally, there are fewer elements involved so slippage and bunching of the dressing are virtually eliminated. Finally, use of the present dressing can obviously be much more cost effective.

Alternatively, the dressing of the present invention may be used in conjunction with another wound or ulcer dressing. In this way the patient still benefits from the better adhesion to moist surfaces, more uniform support, reduced slippage and the care to the surrounding skin provided by the adhesive support bandage.

The extensible bandage can be of any of the compression and support bandages known in the art. For example, woven crepe bandages can be employed. Preferably an elasticated bandage is used. Woven, elasticated compression and support bandages for use in the present dressing can be any of the commercially available products (listed in detail above) typically having elastic yarns surrounded by and woven with non elastic material, such as cotton or synthetics, e.g., polyester. Such products include Ace Bandage (Becton Dickinson), Elastocrepe (Smith & Nephew) and Elastic Bandage (Kendall).

As described above, the hydrocolloid adhesive composition can be of any medical grade adhesive and is preferably a homogeneous blend of mineral oil, one or more polyisobutylenes or mixture of one or more polyisobutylenes and an elastomer such as butyl rubber, styrene radial or block type copolymers, water soluble hydrocolloid gums, water swellable cohesive strengthening agents, and a tackifier. Optionally, zinc oxide may be included. In addition, small amounts of various other optional ingredients can be included. The polyisobutylene component of the pressure sensitive adhesive composition functions to provide adhesion to dry body surfaces, i.e., dry tack, and holds the entire composition together. Preferably, the polyisobutylenes employed are one or more low molecular weight polyisobutylenes having a viscosity average molecular weight of from about 36,000 to about 58,000 (Florey). Such polyisobutylenes are commercially available under the trademark Vistanex from Exxon as grades LM-MS and LM-MH. Optionally, in order to increase the elasticity, tear resistance, and cohesiveness of the adhesive compositions as indicated by a reduction in the cold flow of the adhesive composition, an elastomeric polymer such as butyl rubber can be blended with the polyisobutylenes. Butyl rubber is a copolymer of isobutylene with a minor amount of isoprene having a viscosity average molecular weight of from about 350,000 to about 450,000 (Florey). The polyisobutylenes and butyl rubber can be blended together on a weight basis of from about 4 parts polyisobutylene to about 1 part butyl rubber to about 1 part polyisobutylene to about 4 parts butyl rubber with about 1 part low molecular weight polyisobutylene to about 2 parts butyl rubber being preferred.

The styrene radial or block copolymer component of the hydrocolloid adhesive composition functions to provide extensibility and both rapid and complete recovery from modular strains to the composition. Particularly suitable styrene copolymers include styrene-butadiene-styrene (S-B-S) and styrene-isoprene-styrene (S-I-S) block type copolymers both of which are commercially available, for example, from Shell Chemical Co. under the tradename Kraton as Kraton 1100, 1101, 1102, 1107, etc. Preferably, one or more styrene-isoprene-styrene (S-I-S) block type copolymers are employed.

The hydrocolloid adhesive composition contain from about 5% to about 30% by weight of polyisobutylenes or blends of polyisobutylenes and an elastomer such as butyl rubber and from about 3% to about 30% by weight of styrene copolymers.

Mineral oil is included within the hydrocolloid adhesive composition to increase the aggressiveness of the bonding without requiring undue pressure in applying the adhesive composition to the body, i.e., "wet grab". The mineral oil also functions to increase the stretchability of the final composition. The mineral oil is present in the adhesive compositions of this at from about 8% to about 40% by weight of the final composition.

One or more water soluble hydrocolloid gums are also included within the adhesive compositions. The water soluble hydrocolloids enable the adhesive compositions to adhere to moist body surfaces, i.e., wet tack. Optionally, one or more water swellable cohesive strengthening agents may also be included within the pressure sensitive adhesive compositions. The cohesive strengthening agents along with the water soluble hydrocolloid gums function to control the rate of hydration of the adhesive compositions and enable them to resist erosion by biological fluids such as urine. Suitable water soluble hydrocolloid gums include sodium carboxymethylcellulose, which is preferred, pectin, gelatin, guar gum, locut bean gum, gum karaya, and mixtures thereof. Suitable water swellable cohesive strengthening agents include finely divided substantially water insoluble cross-linked sodium carboxymethylcellulose such as that commercially available under the trademark AcDiSol or Aqualon and available commercially from Hercules Corp. or FMC or that described in U.S. Pat. No. 3,589,364, finely divided substantially water insoluble starch-acrylonitrile graft copolymer such as that described in U.S. Pat. No. 3,661,815 and commercially available from the Grain Processing Corp., and finely divided substantially water insoluble cross-linked dextran such as that commercially available under the trademark Sephadex. The preferred water swellable cohesive strengthening agent is cross-linked sodium carboxymethylcellulose.

The water soluble hydrocolloid gums are present at from about 15% to about 65% by weight of the adhesive compositions and the water swellable cohesive strengthening agents are present at up to about 15% by weight of the adhesive compositions provided that the water soluble hydrocolloid gums and cohesive strengthening agents together are present at from about 15% to about 65% by weight of the adhesive compositions.

The hydrocolloid adhesive compositions also include from about 7.5% to about 15% by weight of a tackifier. Suitable tackifiers include the pentaerythritol esters of rosin commercially available from Hercules under the trademark Pentalyn H, trimethylol propane ester of rosin commercially available from Hercules under the tradename Staybelite Ester 10, and the beta pinine resins such as Piccolyte S 115 or the cyclopentadiene resins commercially available from Exxon such as Escorez 5300 or the Arakawa cyclic tackifiers namely the Arkon products.

Skin protective agents, such as zinc oxide, may be present in amounts up to about 20 percent by weight of the total composition.

Small amounts, i.e., less than about 5% by weight of the adhesive composition, of other optional ingredients may be included in the adhesive composition. For example, up to about 0.5% by weight of an antioxidant such as zinc dibutylithiocarbamate (commercially available from R. T. Vanderbilt Co. under the tradename Butyl Zimate) or those available form Ciba Geigy such as Irganox 1010, tetrakis [methylene(3,5-ditert-butyl-4-hydroxyhydrccinnamate)methane], or Irganox 1076, octadecyl 3-[3,5-ditert-butyl-4'-hydroxy-phenyl]propionate, a deodorant such as chlorophyllins, or a perfume agent may be included. In addition, small amounts of a pharmacologically active ingredient can be included in the adhesive composition, for example, an antibiotic or antimicrobial agent such as neomycin, an antiseptic agent such as povidone iodine, or an antiinflammatory agent such as hydroortisone or triamcinolone acetonide may be included. When the bandage is used as a burn dressing, small amounts of active ingredients such as silver sulfadiazine, sulfadiazine, and other silver compounds can be included in the composition. Also, small amounts, i.e., less than 1% by weight of the adhesive composition, of physical reinforcing agents that form Van der Walls bonds with the polymeric substituents can be included such as carbon black, polyaramids (commercially available under the tradename Kevlar), hydrated silicas, etc.

The adhesive compositions are prepared by combining the polyisobutylenes, optional butyl rubber, styrene copolymers, mineral oil, and antioxidant with heating and agitation in a heavy duty high shear sigma blade or equivalent type mixer. The mixture is heated from about 120° to about 150° C. with temperatures of 135° C. required when butyl rubber is present in the composition and mixing is continued until the mass is homogeneous. The mixture is then cooled and the tackifier is added with mixing at about 100° C. The water soluble gums, water swellable cohesive strengthening agents, mineral oil, and the other optional ingredients are added with continued heating and mixing at about 80° to 90° C. The resultant homogeneous mass is then extruded and rolled or pressed to desired thickness. Any thickness can be employed, however, thicknesses 5 mils or above are preferred for the adhesive composition.

The so-produced thin hydrocolloid adhesive composition can next be laminated onto one side of an extensible bandage and a release paper may be conveniently employed on the surface of the adhesive composition which is ultimately applied to the skin. In one embodiment an elasticated, woven bandage is coated, prior to the lamination process, on the adhesive composition-receiving side with a thin film of latex or similar adhesive to improve the cohesive properties of the finished product.

While the dressings of the present invention can be employed in any convenient shape and size, they are typically in the form of a long ribbon-type bandage being stored and applied from a rolled form. Such dressings are typically 3 to 4 inches wide and 5 to 6 yards long when stretched.

Although the composite compression and support dressings have been described primarily with regard to the treatment of venous leg ulcers, it should be understood that this dressing could be employed in any situation where an occlusive, flexible, elastic compression and support article having a fluid-interactive dressing surface is required. The present dressing is usable alone or as a support/protection wrap to cover a different primary dressing.

The dressings of the present invention can be sterilized, for example, by means of gamma radiation.

The present invention will now be further described by reference to the following example, however, the invention is not meant to be limited to the details therein.

EXAMPLE

A. Hydrocolloid Composition

|  | Percent by Weight |
|---|---|
| Polyisobutylene (Vistanex LM-MH) | 9.6 |
| Sodium carboxymethylcellulose | 26.0 |
| Cross-linked sodium carboxymethylcellulose (Ac-Di-Sol) | 9.3 |
| Mineral Oil | 20.4 |
| Styrene-isoprene-styrene Copolymer (Kraton D1107) | 20.4 |
| Antioxidant (Irganox 1010) | 1.5 |
| Tackifier (Pentalyn H) | 12.8 |

The mineral oil (22.44 kg), polyisobutylene (10.56 kg), Kraton 1107 (22.44 kg) and Irganox 1010 (1.65 kg) were combined in a sigma blade mixer with heating (115° C.) and agitating for about 1.5 hours. The mixture was cooled to about 100° C. and after another 30 minutes of blending, the sodium carboxymethylcellulose (28.60 kg), cross linked sodium carboxymethylcellulose (10.23 kg) and Pentalyn H (14.08 kg) were added. The mixing was thereafter continued for another 30 minutes at 100° C. until a homogeneous mass is obtained. The mass was allowed to cool and was flattened to 10 mils in thickness. Silicone release paper was applied to one side and the flattened mass was cut into 4 inch wide strips.

B. Composite Compression and Support Dressing

An elasticated 4 inch woven bandage (Bandage available from Edward Weck & Sons) was coated on one side with a thin film of a latex. The exposed surface of the hydrocolloid adhesive strip prepared in Part A was extrusion laminated to the latex coated surface of the Bandage. The so-formed composite compression and support dressing was wound onto a 0.05 inch diameter by 4 inch long core.

What is claimed is:

1. An extensible compression and support dressing comprising:

an extensible bandage of suitable size and shape to facilitate wrapping said bandage spirally around an affected body part; and, a thin, fluid interactive extensible hydrocolloid adhesive composition laminated to one side of said bandage.

2. The dressing of claim 1 wherein said extensible bandage is a woven, elasticated bandage.

3. The dressing of claim 1 wherein said fluid-interactive hydrocolloid adhesive composition comprises a substantially homogeneous mixture of from about 5 to about 30 percent by weight of one or more polyiosubtylenes or a blend of one or more polyisobutylenes and butyl rubber, from about 3 to about 30 percent by weight of one or more styrene radial or block type copolymers, from about 8 to about 40 percent by weight of mineral oil, from about 15 to about 65 percent by weight of one or more water soluble hydrocolloid gums, up to about 15 percent by weight of one or more water swellable cohesive strengthening agents provided that said water soluble hydrocolloid gums and said water swellable cohesive strengthening agents together are present at from about 15 to about 65 percent by weight of said composition, from about 7.5 to about 15 percent by weight of a tackifier, and up to about 5 percent by weight of optional ingredients selected from antioxidants, deodorants, medicaments, skin protective agents and reinforcing agents.

4. The dressing of claim 1 further comprising a latex adhesive layer interposed said bandage and said hydrocolloid adhesive composition to provide cohesion therebetween.

5. An adhesive composition of claim 1 wherein said water soluble hydrocolloid is selected from the group consisting of sodium carboxymethylcellulose, pectin, gelatin, guar gum, locust bean gum, gum karaya, and mixtures thereof and said water swellable cohesive strengthening agent is selected from the group consisting of cross-linked sodium carboxymethylcellulose, starch-acrylonitrile graft copolymers, and cross-linked dextran.

6. An adhesive composition of claim 5 wherein said styrene copolymer is a styrene-isoprene-sytrene or a styrene-butadiene-styrene block polymer.

7. An adhesive composition of claim 6 wherein said styrene copolymer is a styrene-isoprene-styrene block copolymer.

8. An adhesive composition of claim 7 wherein said polyisobutylenes are one or more low molecular weight polyisobutylenes.

9. A method of treating wounds in a mammalian specie comprising applying the composite compression and support dressing of claim 1 to the affected area of said specie, whereby compression, support, adhesion to moist surfaces and care to skin surrounding said wound are provided.

10. The method of claim 9 wherein said dressing is employed in conjunction with one or more other wound dressing materials or articles.

11. A method of treating venous stasis leg ulcers in a mammalian specie comprising applying the composite compression and support dressing of claim 1 to the affected area of said specie, whereby compression, support, adhesion to moist surfaces and care to skin surrounding said ulcer are provided.

12. The method of claim 11 wherein said dressing is employed in conjunction with one or more other leg ulcer dressing materials or articles.

* * * * *